(12) United States Patent  (10) Patent No.: US 7,619,130 B2
Nielsen et al.                (45) Date of Patent:    Nov. 17, 2009

(54) MULTI-LAYER WOUND DRESSING FORMED AS A SINGLE UNIT

(75) Inventors: John Stern Nielsen, Allerod (DK); Mette Irene Kolte, Soborg (DK); Borge Gundersen, Tikob (DK)

(73) Assignee: Coloplast A/S, Humlebaek (DK)

( * ) Notice: Subject to any disclaimer, the term of this patent is extended or adjusted under 35 U.S.C. 154(b) by 128 days.

(21) Appl. No.: 10/312,568

(22) PCT Filed: Jul. 9, 2001

(86) PCT No.: PCT/DK01/00480

§ 371 (c)(1),
(2), (4) Date: Jan. 13, 2003

(87) PCT Pub. No.: WO02/05737

PCT Pub. Date: Jan. 24, 2002

(65) Prior Publication Data

US 2003/0153860 A1     Aug. 14, 2003

(30) Foreign Application Priority Data

Jul. 18, 2000 (DK) ............................ 2000 01112

(51) Int. Cl.
    *A61F 13/00* (2006.01)
(52) U.S. Cl. .................... 602/58; 602/41; 602/42; 602/54
(58) Field of Classification Search ............ 602/41–59; 128/888, 889; 604/304–308; 606/213–216
    See application file for complete search history.

(56) References Cited

U.S. PATENT DOCUMENTS

| 3,419,006 | A |   | 12/1968 | King ......................... 128/268 |
| 3,972,328 | A |   | 8/1976  | Chen |
| 4,367,732 | A |   | 1/1983  | Poulsen et al. ............. 128/156 |
| 4,538,603 | A |   | 9/1985  | Pawelchak et al. |
| 4,552,138 | A |   | 11/1985 | Hofeditz et al. ............. 128/156 |
| 4,860,737 | A | * | 8/1989  | Lang et al. ................... 602/43 |
| 4,867,748 | A |   | 9/1989  | Samuelsen ................. 604/336 |
| 4,909,243 | A | * | 3/1990  | Frank et al. ................... 602/58 |
| 5,051,259 | A |   | 9/1991  | Olsen et al. ................. 424/443 |
| 5,086,763 | A |   | 2/1992  | Hathman ..................... 602/42 |
| 5,086,764 | A |   | 2/1992  | Gilman ........................ 602/42 |
| 5,133,821 | A |   | 7/1992  | Jensen ........................ 156/245 |
| 5,354,261 | A |   | 10/1994 | Clark et al. .................. 602/58 |
| 5,409,472 | A | * | 4/1995  | Rawlings et al. ........... 604/307 |
| 5,431,622 | A | * | 7/1995  | Pyrozyk et al. ................ 602/2 |
| 5,512,041 | A | * | 4/1996  | Bogart ........................ 602/58 |
| 5,556,375 | A |   | 9/1996  | Ewall ......................... 602/58 |

(Continued)

FOREIGN PATENT DOCUMENTS

EP         0 206 646        12/1986

(Continued)

*Primary Examiner*—Kim M Lewis
(74) *Attorney, Agent, or Firm*—Jacobson Holman PLLC

(57) ABSTRACT

A wound dressing comprising a backing layer, a skin facing layer and an absorbent layer between the backing layer and the skin facing layer, characterised in that at least a part of the absorbent layer is adjacent to the backing layer, the backing layer and the absorbent layer are mutually displaceable, and that the skin facing layer is located at the skin facing surface of the backing layer.

21 Claims, 2 Drawing Sheets

U.S. PATENT DOCUMENTS

| | | |
|---|---|---|
| 5,607,388 A | 3/1997 | Ewall ............ 602/58 |
| 5,632,731 A * | 5/1997 | Patel ............ 602/59 |
| 5,643,187 A | 7/1997 | Naestroft et al. ............ 602/43 |
| 5,681,579 A * | 10/1997 | Freeman ............ 424/448 |
| 5,714,225 A | 2/1998 | Hansen et al. |
| 6,191,335 B1 * | 2/2001 | Robinson ............ 602/41 |

FOREIGN PATENT DOCUMENTS

| | | |
|---|---|---|
| EP | 0 236 104 | 9/1987 |
| EP | 0 264 299 | 4/1988 |
| EP | 0 272 149 A2 | 6/1988 |
| EP | 0 352 086 | 1/1990 |
| EP | 0 415 183 | 3/1991 |
| EP | 0 641 553 | 3/1995 |
| GB | 1 280 631 | 7/1972 |
| GB | 1 586 182 | 3/1981 |
| WO | 91/01706 | 2/1991 |
| WO | 92/16245 | 10/1992 |
| WO | 97/07759 | 3/1997 |
| WO | WO 97/46265 | 12/1997 |
| WO | 98/31402 | 7/1998 |
| WO | 99/08724 | 2/1999 |

* cited by examiner

MULTI-LAYER WOUND DRESSING FORMED AS A SINGLE UNIT

This is a nationalization of PCT/DK01/00480 filed Jul. 9, 2001 and published in English.

FIELD OF THE INVENTION

The invention relates to a wound dressing, especially a wound dressing being suitable for handling exuding wounds.

BACKGROUND OF THE INVENTION

Wound dressings with layers for absorbing body fluids are known in the art. Absorbent layers are provided for the uptake of body fluids, especially wound exudate, so as to enable the wound dressing to keep a constant moist environment over the wound site, and at the same time avoiding maceration of the skin surrounding the wound.

Much effort has been directed to enhancing the rate of uptake and capacity of the wound dressing, in particular the absorbent layer, to uptake body fluids. Absorbent layers in wound dressings have comprised hydrocolloid, super absorbents, foams and synthetic materials which have extensive capacity to absorb body fluids, especially wound exudate.

However, increasing the capacity and rate of fluid uptake within a wound dressing may give rise to problems, both in assuring that the body fluids do not migrate from the wound dressing and in assuring the wound does not dry out.

Hydrocolloid dressings are some of the most efficient and mostly used dressings, being skin-friendly, absorbent and capable of creating moist wound healing conditions. However, when used on some exuding wounds, the absorption rate tends to be too low. The advantages of the hydrocolloid dressing is the ability of creating a moist wound healing environment and acting as a barrier against bacteria.

A frequent problem when treating exuding wounds is maceration. Usually the absorbent part of the dressing is optimised to substantially vertical absorption, so that the skin surrounding the wound is not exposed to the exudate in order to avoid maceration of this healthy, but fragile skin. However, these properties are limiting the absorption capacity of the dressing to the part of absorbent material being directly over the wound. Barrier cream/skin conditioning paste, such as zinc paste, may be used on the surrounding skin in order to avoid the maceration, but the paste will often inhibit both the adhesive tack of the dressing as well as the ability of absorbing exudate.

Highly exuding wounds are often treated with foams or alginate, which are capable of absorbing high amounts of exudate but requires additional cover dressings, as well as the risk of maceration is high. The retention of foam is low, which may be a problem when used on body parts being exposed to pressure.

A way of overcoming the problems with limited absorption capacity is to create a dressing with high permeability. This is usually done by using a backing layer being more permeable to vapour, but still liquid and bacteria impermeable. Using such a film the absorption capacity will rise when the permeability rises, enhancing the absorption capacity of the dressing. The capacity rises due to evaporation of moisture through the backing layer.

Various absorbent dressings are known:

From International Patent Application No. WO A 99/08724 is known a dressing comprising multiple layers. A wound contacting layer, being substantially free from adhesive and hydrocolloids, gelling and absorbing layers and a hydrophobic backing layer. The layers are joined by lamination, using pressure and heat.

U.S. Pat. No. 5,086,764 discloses a wound dressing with an adhesive base sheet at the skin facing side, on top of the base sheet an absorbent pad, the top surface of the pad having a hydrophobic backing. The base sheet has a central aperture over the wound site in order to allow quick uptake of wound exudate into the absorbent pad. On top of the absorbent pad may be a top film for fixation. It is possible to remove the top film and change the absorbent pad without detaching the base sheet from the skin. The hydrophobic backing of the absorbent pad provides a bacteria proof barrier. The reference is silent with respect to the vapour permeability of this barrier. The hydrophobic coating is preferably a fluorocarbon such as SCOTCHGARD, which has a low vapour permeability.

European Patent Application No. EP A1 641 553 discloses a securement for a wound dressing, in which an adhesive frame is mounted around the wound, an absorbent pad is placed over the wound and then a cover layer is placed on top. The cover layer is fixed detachably to the adhesive frame. Thus, the wound dressing is in the form of an assembly.

In International Patent Application No. WO 91/01706 is shown a wound dressing comprising a vapour permeable top film, over an absorbent foam pad, and an skin-contacting adhesive layer with an aperture over the wound. The top film is laminated to the foam pad.

European Patent Application No. EP A1 236 104 discloses a wound dressing with an adhesive foam frame on top of which a film and an absorbent pad is fixed.

International Patent Application No. WO A 98/31402 discloses a wound dressing comprising a perforated wound contacting layer such as a film or a net, a backing layer, and between these two layers is a fibrous absorbent layer. The absorber and the backing layer are combined by heat-lamination.

International Patent Application No. WO A 97/07759 discloses a wound dressing comprising a backing layer partly being coated with adhesive. The adhesive coating is in the form of a pattern in which the percentage of adhesive in the marginal region is higher than in the central region. The dressing may further comprise an absorbent material in the form of a hydrogel or alginate.

When using highly permeable films in dressings the different parts of the dressing are combined, usually by coating the backing, fully or partly, with adhesive, in order to keep the dressing together. The adhesive coating will however, decrease the permeability of the film significantly. Another way of producing such a dressing is to combine the layers of the dressing by lamination. However, the heat and pressure of the lamination process may change the permeability properties of the backing layer, as well as the structure of the absorbent layer may be crushed.

The flexibility of a dressing wherein the layers are tied together by adhesive or lamination may also be reduced, enhancing the risk of handling problems and leakage when used on curved body parts.

Thus, there is still a need for a flexible, highly absorbent wound dressing being capable of absorbing large amounts of wound exudate without giving rise to maceration.

BRIEF DESCRIPTION OF THE INVENTION

The present invention relates to a wound dressing comprising a backing layer, a skin facing layer and an absorbent layer between the backing layer and the skin facing layer.

BRIEF DESCRIPTION OF THE DRAWINGS

The invention is explained more in detail with reference to the drawings in which.

DETAILED DESCRIPTION OF THE INVENTION

Figure 1:
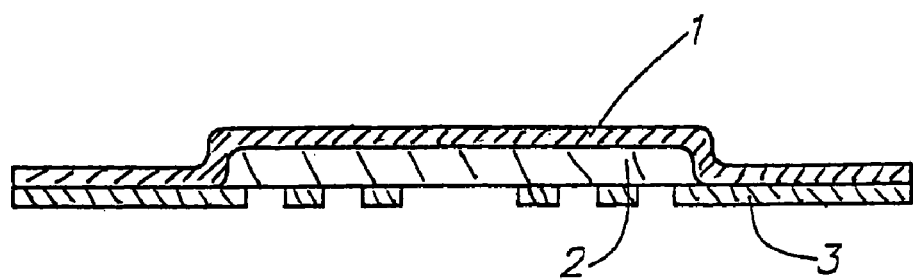
FIG. 1 shows a cross-section of an embodiment of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a wound dressing comprising a backing layer, a skin facing layer and an absorbent layer between the backing layer and the skin facing layer, characterised in that the skin facing layer is an adhesive layer, that the adhesive layer secures the absorbent layer to the backing layer and that the adhesive layer is interrupted in at least one zone enabling a direct contact between the absorbent layer and the backing layer and exposing at least a part of the skin contacting surface of the absorbent layer.

A dressing according to the present invention is thus in the form of a single unit, not an assembly. The dressing will provide a high initial absorption due to the direct contact between the wound and the absorbent pad, and a high absorption capacity due to the lack of adhesive or lamination between the backing layer and the absorbent layer combined with a high permeability of the backing layer. A dressing in a single unit decreases the risk of leakage compared to an assembled or reopenable dressing. The adhesive will provide a tight fit of the dressing to the skin and at the same time protect the surrounding skin from maceration from the wound, while the absorbent layer will absorb wound exudate and transport it away from the wound by evaporating it from the top of the dressing.

In a preferred embodiment of the invention the backing layer and the absorbent layer are "mutually displaceable" such that there is free movement of the backing layer relative to the absorbent layer.

By locating the backing layer and the absorbent layer adjacent to each other and mutually displaceable, an enhanced flexibility and permeability is obtained. The flexibility is enhanced due to the higher bending and twisting flexibility, as well as when the absorbent layer absorbs exudate and thereby expands, the free movement of the backing layer will allow more space over the expanding region of the absorbent layer and thus a larger surface for evaporation.

If the backing layer is coated, fully or partly with adhesive, the permeability of the backing layer will decrease. When lamination is used instead, the influence of heat and/or pressure may disrupt the permeability qualities of the backing layer, as well as the absorber, which often is a fragile matrix structure, may be damaged.

The highest possible permeability of the backing layer is obtained when no adhesive is applied between the backing layer and the absorbent layer. By avoiding, or diminishing the use of adhesive or lamination, a maximum permeability of moisture from the absorbent layer to the environment is achieved.

In one embodiment of the invention all of the non-skin-facing surface of the absorbent layer is adjacent to the backing layer.

The skin facing layer may extend over a part of the surface between the absorbent layer and the backing layer.

The backing layer and the absorbent layer may have connection points or lines. The points or lines may be achieved by dots or lines of adhesive or they may be created by welding. It is preferred that the points or lines are arranged in such a way that at least a part of the backing layer and the absorbent layer are still mutually displaceable.

The skin facing layer may cover at least a fraction of the skin facing surface of the absorbent layer. The skin facing layer may fully cover the skin facing surface of the absorbent layer or the layer may be coated in a pattern or with one or more apertures or slits.

The skin facing layer may comprise an aperture in the area covering the absorbent layer. The aperture may especially be located centrally over the wound and will render it possible to have a fast absorption as the absorbent layer will be in direct contact with the exudate, as the exudate will not have to pass through the skin facing layer first.

The apertures may be in the form of a pattern of smaller or larger apertures. Preferably the apertures are in the area of the skin facing layer under the absorbent layer.

Preferably the aperture has about the same dimensions as of the wound. This will enhance the absorption rate over the wound, while the fragile skin next to the wound will be protected by the skin facing layer.

The aperture in the skin facing layer may be enlarged to adapt to the size of the wound. The enlargement may be done by scissors or by the use of pre-cuts lines in the skin facing layer, enabling easy removal of excess skin facing layer before application. The pre-cuts lines may e.g. be in the form of concentric circles, squares, or a helix.

The skin facing layer may comprise a reinforcing layer. The reinforcing layer may be in the form of a web or a net, or a non woven, fibres, etc. The reinforcing layer may ease the handling during application and removal as well as the strength of the dressing is enhanced. When the absorbent layer absorbs exudate the skin facing layer will be wetted not only from the skin facing side but also from the top side, by absorbed exudate from the absorbent layer. This may alter the strength properties of the skin facing layer, and demand for a strengthening layer.

The absorbent layer may comprise an exudate distributing material. To have full benefit of the absorbent material in the absorbent layer a liquid distributing layer, acting as a wick, may be incorporated in the dressing. The wicking layer renders it possible to utilise the areas of absorbent layer not being located right above the wound as well as the wetted surface of the absorbent layer will be enlarged and thus the evaporation through the backing layer will be enhanced.

The absorbent layer may be in the form of one or more layers, e.g. a multilayer, comprising layers of different absorption properties in order to optimise the absorption capacity of the absorbent layer.

The absorbent layer may be in the form of a matrix structure, e.g. with incorporated particles.

When the absorbent layer comprises a material capable of distributing the absorbed exudate, full utilisation of the absorption capacity in the dressing may be obtained.

The absorbent layer may comprise any absorbent material known per se being suitable for use in wound care devices, e.g. polyacrylate, CMC, cellulose or derivatives thereof, gums, foam or alginate.

A material being capable of retaining and/or distributing the liquid is preferred.

The absorbent layer may comprise super absorbent particles (SAP) and/or super absorbent fibres (SAF).

The absorbent layer may comprise a horizontally spreading/absorbent layer.

The feature of horizontal absorption and/or spreading of exudate is contrary to normal practice in absorbent wound dressings, as the perception of a good dressing is vertical absorption in order to avoid the skin surrounding the wound being exposed to the exudate. In the dressing of the present invention horizontal spreading is not a problem because the surrounding skin is protected by the skin facing layer.

In one embodiment of the invention the absorbent layer may comprise spheres or inclusions of absorbent material, in a structure like pearls on a string. Between the pearls a material capable of distributing the wound exudate is located.

The skin facing surface of the absorbent layer may be covered by a stop layer for preventing any speck or fluff from the absorbent layer to enter the wound. The stop layer may be of any suitable material known in the art being capable of retaining absorbent material, such as a web or net, non-woven or a perforated polymeric film, knits, PP, PE, polyester or lycra.

The absorbent layer may be embossed or pre-cut in order to enhance flexibility of the dressing.

The backing layer may be liquid impervious but vapour permeable or it may be of a type having a higher water permeability when in contact with liquid water than when not in contact. The backing layer may be of any suitable material known per se for use in the preparation of wound dressings e.g. a foam, a nonwoven or a polyurethane, polyethylene, polyester or polyamide film.

A suitable material for use as a backing layer is a polyurethane. A preferred low friction film material is disclosed in U.S. Pat. No. 5,643,187.

The skin facing layer may be a layer of adhesive, hydrocolloid, hydrogel, foam, polymer gel, alginate or any other skin-friendly material. The layer may constitute all of the skin-contacting surface, or only a part thereof. Other suitable materials may be non-wovens, knits, PP, PE, polyester, lycra or material capable of retaining SAP.

In a preferred embodiment of the invention the skin facing layer comprises an adhesive.

The adhesive may be any skin-friendly adhesive known per se, e.g. an adhesive comprising hydrocolloids or other moisture absorbing constituents for prolonging the time of use. The adhesive may suitably be of the type disclosed in GB patent specification No. 1 280 631, in DK patent specifications Nos. 127,578, 148,408, 154,806, 147,226 and 154,747, in EP published application Nos. 0 097 846 and 0 415 183, in SE published application No. 365,410, in WO publication No. 88/06894, in U.S. Pat. No. 4,867,748, and in NO published application No. 157,686. Especially preferred are the adhesives disclosed in U.S. Pat. Nos. 4,367,732 and 5,051, 259 and DK patent specification No. 169,711.

In a preferred embodiment of the invention the adhesive comprises a hydrocolloid adhesive. The use of a hydrocolloid adhesive may provide an excellent protection of the surrounding skin of the wound by inducing the moist wound healing environment, and yet avoiding maceration.

Furthermore, when exudate is spread in the absorbent layer it leads to wetting of the adhesive layer from the side opposite the skin. When hydrocolloid adhesive becomes moist it looses adhesive power. Hence, wetting of the adhesive from the back side leads to weaker adhesive tack i.e. the adhesion to the skin is lowered or simply turned off, the degree of loss of adhesive tack is depending on amount of exudate. In this way easy removal of the dressing without stressing the wound and skin is facilitated.

The skin facing layer may also comprise any other adhesives, chosen from a wide range of different types of adhesives including for instance the acrylic types, and types derived from polyisobutylene (PIB), polyurethanes, EVA-compounds, amorphous poly alpha olefins (APAO's), silicones, polyvinyl ether, etc.

A dressing of the invention may have bevelled edges in order to reduce the risk of "rolling-up" the edge of the dressing reducing the wear-time and thus disturbing and prolonging the healing of wounds or e.g. cracks normally healing slowly due to physical stress. A bevelling may be carried out discontinuously or continuously in a manner known per se e.g. as disclosed in EP patent No. 0 264 299 or in U.S. Pat. No. 5,133,821.

The adhesive surface of the dressing may be protected by a protective cover or a release-liner before application. The protective cover or release liner will typically be siliconised thermoplastic films based on for example polyolefins such as polyethylene, polypropylene or the like or it may be siliconised paper.

The dressing according to the invention may comprise an active ingredient.

The wound dressing according to the invention may comprise one or more active ingredients, e.g. a pharmaceutical medicament. This opens for a combined medical treatment of a wound, where the dressing absorb wound exudate and the pharmaceutical medicaments will be applied to the wound. The pharmaceutical medicaments will either be incorporated in the wound dressing or migrate to the wound surface and promote its function.

Examples of such pharmaceutical medicaments includes a cytochine such as a growth hormone or a polypeptide growth factor such as TGF, FGF, PDGF, EGF, IGF-1, IGF-2, colony stimulating factor, transforming growth factor, nerve stimulating growth factor and the like giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorhexidine, silver salts such as sulphadiazine, silver nitrate, silver acetate, silver lactate, silver sulphate, silver sodium thiosulphate or silver chloride, zinc or salts thereof, metronidazol, sulpha drugs, and penicillin's, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as lidocaine or chinchocaine, emollients, retinoids or agents having a cooling effect which is also considered an aspect of the invention.

The active ingredient may also comprise odour controlling or odour reducing material.

The skin facing layer may be impregnated with zinc-paste or other skin-conditioning or healing enhancing materials.

The skin facing layer may be capable of adsorption or absorption and retention of high molecular parts of the wound exudate, e.g. proteins. The handling may be in the form of a mechanical collection of wound exudate in e.g. a three-dimensional non-woven, a loosely knitted or woven material, a fleece material, a material with a wavy surface, or a filament material like a rya, or it may be chemically, by binding the high molecular parts of the wound exudate, or it may be enzymatically by degrading the high molecular parts of the wound exudate.

The skin facing layer may also comprise non-protein bonding zones, through which the fluid is absorbed without clogging because of the proteins.

The absorbent layer may be softened by incorporation of glycerine.

DETAILED DESCRIPTION OF THE DRAWINGS

In FIG. 1 is shown one embodiment of the invention. The dressing comprises a backing layer (1) adjacent to an absorbent layer (2) and a skin facing layer (3) covering at least a part of the skin facing surface of the dressing. A part of the skin facing surface of the absorbent layer is left without the skin facing layer in order to facilitate rapid uptake of exudate from the wound.

Figure 2:
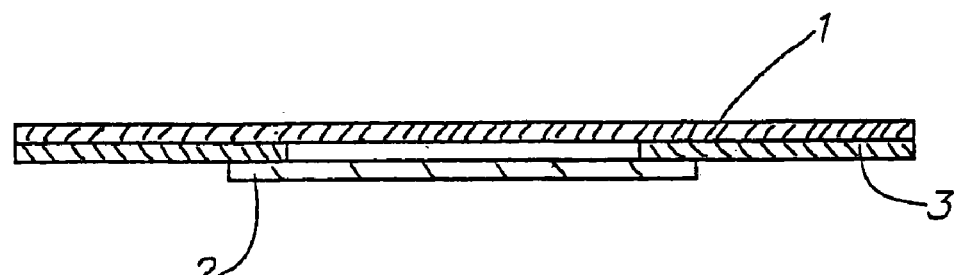
FIG. 2 shows a cross-section of another embodiment of the invention.

In FIG. 2 is shown another embodiment of the invention, in which the skin facing layer (3) extends into the interspace between the backing layer (1) and the absorbent layer (2). In this embodiment of the invention the skin facing surface of the absorbent layer is not covered with a skin facing layer leaving the absorbent layer in direct contact with the wound site.

Figure 3:
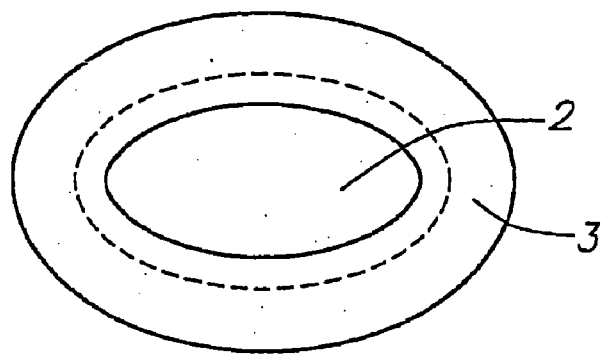
FIG. 3 shows a top view of a third embodiment of the invention.

FIG. 3 shows a third embodiment of the invention shown from above, with the skin facing surface up. The skin facing layer (3) is located at the skin facing surface of the backing layer and extends over the edge portion of the absorbent layer (2). The centre of the skin facing layer defines an aperture under the absorbent layer. The size of the aperture may be enlarged, e.g. by cutting with a pair of scissors, in order to costumize the size of the aperture to the size of the wound. When the skin facing layer comprises an adhesive, an intermediate layer of approximately the same size of the absorbent layer may be located between the adhesive layer and the absorbent layer. The intermediate layer prevents the adhesive from adhering to the absorbent layer rendering removal of excess adhesive layer without damaging the absorbent layer possible. This intermediate layer may be any suitable material such as a non-woven, a permeable film or a foam.

Figure 4:
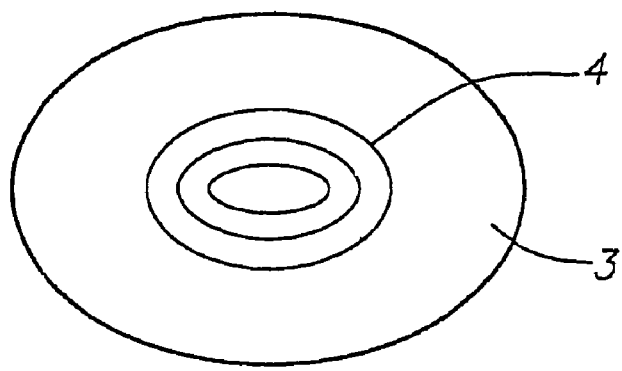
FIG. 4 shows a top view of a fourth embodiment of the invention.

An fourth embodiment of the invention is shown in FIG. 4. The skin facing layer (3) is covering the skin facing surface of the dressing. In the part of the skin facing layer covering the absorbent layer there are pre-cut lines (4) carving up the central part of the skin facing layer into concentric circles. Before application of the dressing a suitable number of the pre-cut concentric circles of skin facing layer is removed in order to adapt the size of the aperture to the size of the wound.

Figure 5:
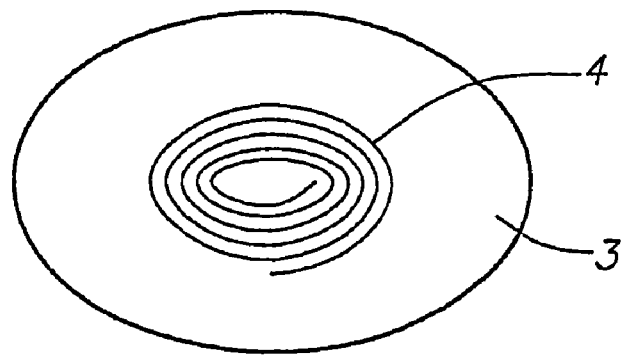
FIG. 5 shows a top view of a fifth embodiment of the invention.

FIG. 5 shows a fifth embodiment of the invention. The central part of the skin facing layer (3) is pre-cut into a helix (4). Before application the centre of the helix is entered and pulled up until the size of the aperture fits the wound. The excess skin facing layer of the helix is removed.

Figure 6:
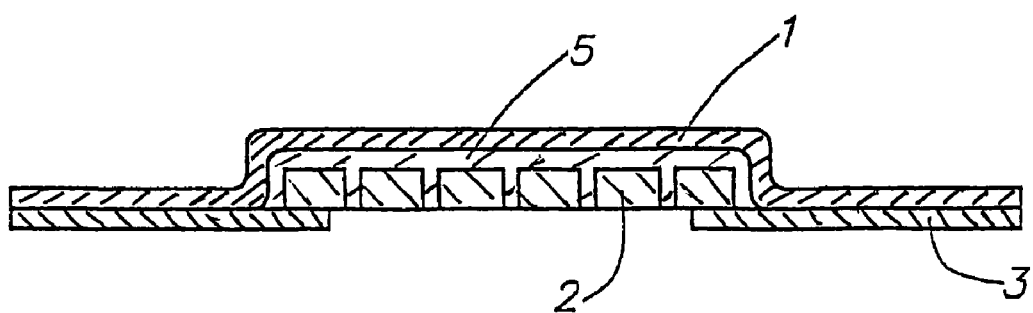
FIG. 6 shows a cross-section of a sixth embodiment of the invention.

In FIG. 6 is shown a sixth embodiment of the invention in which the absorbent layer (2) comprises a liquid distributing layer (5). The distributing layer is connected to the wound contacting surface through channels or wicks of liquid distributing material, enabling the distributing layer to absorb fluid and transport and distribute the fluid to the upper part of the dressing, and by spreading the moisture enhancing the evaporation through the backing layer. Thus, the absorbent capacity of the dressing is enhanced.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A wound dressing comprising a backing layer, a skin facing layer and an absorbent layer between the backing layer and the skin facing layer, said backing layer and said absorbent layer being mutually displaceable such that there is free movement of said backing layer relative to said absorbent layer, said skin facing layer including at least one aperture in an area covering said absorbent layer, and said skin facing layer being substantially adhesive against the skin in use and securing the absorbent layer to the backing layer such that said dressing is a single unit.

2. The wound dressing as set forth in claim 1, wherein said absorbent layer is in direct contact with said backing layer.

3. The wound dressing as set forth in claim 1, wherein said absorbent layer includes multiple layers therein having different absorbent properties.

4. The wound dressing as set forth in claim 1, wherein all of a non-skin-facing surface of said absorbent layer is adjacent said backing layer.

5. The wound dressing as set forth in claim 1, wherein said skin facing layer includes an adhesive surface protected by a cover.

6. The wound dressing as set forth in claim 5, wherein said cover is a release liner.

7. The wound dressing as set forth in claim 1, wherein said skin facing layer includes pre-cut lines for adapting a size of said aperture.

8. The wound dressing as set forth in claim 1, wherein said skin facing layer includes a reinforcing layer.

9. The wound dressing as set forth in claim 1, wherein said absorbent layer includes an exudate distributing material.

10. The wound dressing as set forth in claim 1, wherein said absorbent layer includes a wicking layer for horizontally spreading absorbed material.

11. The wound dressing as set forth in claim 1, wherein said backing layer is vapor permeable but impermeable to liquids.

12. The wound dressing as set forth in claim 1, wherein said adhesive of said skin facing layer is a hydrocolloid adhesive.

13. The wound dressing as set forth in claim 1, wherein said dressing includes at least one active ingredient.

14. The wound dressing as set forth in claim 1, wherein there is no adhesive or lamination between the backing layer and the absorbent layer.

15. The wound dressing as set forth in claim 1, wherein only dots or lines of adhesive or lamination are provided between the backing layer and the absorbent layer such that at least part of said backing and absorbent layers remain mutually displaceable.

16. The wound dressing as set forth in claim 1, wherein said skin facing layer connects only edge portions of said backing layer and said absorbent layer.

17. A wound dressing comprising a backing layer, a skin facing layer and an absorbent layer in the form of a single unit, said backing layer and said absorbent layer being mutually displaceable such that there is free movement of said backing layer relative to said absorbent layer, at least part of said absorbent layer being adjacent said backing layer, and said skin facing layer being substantially adhesive against the skin in use and located at a skin facing surface of said backing layer.

18. The wound dressing as set forth in claim 17, wherein there is no adhesive or lamination between the backing layer and the absorbent layer.

19. A wound dressing comprising a backing layer, a skin facing layer and an absorbent layer between the backing layer and the skin facing layer, said backing layer and said absorbent layer being adjacent one another and mutually displaceable for enhanced permeability, said absorbent layer absorbing exudate and thereby expanding in a region thereof and free movement of said backing layer relative to said absorbent layer allowing more space over said expanding region, said skin facing layer being substantially adhesive against the skin in use and securing the absorbent layer to the backing layer such that said dressing is a single unit.

20. The wound dressing as set forth in claim 19, wherein said skin facing layer includes at least one aperture in an area covering said absorbent layer.

21. A wound dressing comprising a backing layer, a skin facing layer and an absorbent layer between the backing layer and the skin facing layer, said backing layer and said absorbent layer being mutually displaceable such that there is free movement of said backing layer relative to said absorbent layer, said skin facing layer including at least one aperture in an area covering said absorbent layer, and said skin facing layer securing the absorbent layer to the backing layer by connecting only edge portions of said absorbent and backing layers such that said dressing is a single unit.

* * * * *